United States Patent
Cady et al.

(10) Patent No.: US 6,340,671 B1
(45) Date of Patent: Jan. 22, 2002

(54) STABLE COMPOSITIONS FOR PARENTERAL ADMINISTRATION AND THEIR USE

(75) Inventors: Susan Mancini Cady, Yardley, PA (US); William David Steber, Ledgewood, NJ (US); Phillip Wayne Hayes, Rushland, PA (US); Mary Ehlers Doscher, Trenton, NJ (US); Kurt Allen Schwinghammer, Richboro, PA (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 08/263,574

(22) Filed: Jun. 22, 1994

Related U.S. Application Data

(63) Continuation-in-part of application No. 07/734,430, filed on Jul. 23, 1991, now abandoned.

(51) Int. Cl.$^7$ ............... A61K 31/70; A61K 9/16
(52) U.S. Cl. .............. 514/28; 514/12; 514/30; 514/450; 514/964; 514/965; 424/490; 424/493; 424/502
(58) Field of Search ............... 514/450, 28, 30, 514/12, 964, 965; 424/490, 493, 502

(56) References Cited

U.S. PATENT DOCUMENTS

| | | | | |
|---|---|---|---|---|
| 4,144,352 A | * | 3/1979 | Putter | 424/279 |
| 5,106,994 A | * | 4/1992 | Carter et al. | 549/264 |
| 5,169,956 A | * | 12/1992 | Carter et al. | 549/264 |
| 5,185,108 A | * | 2/1993 | Shimandle | 264/11 |
| 5,192,546 A | * | 3/1993 | Abercrombie | 425/405 |
| 5,213,810 A | * | 5/1993 | Steber | 424/490 |
| 5,346,698 A | * | 9/1994 | Abercrombie | 424/405 |

FOREIGN PATENT DOCUMENTS

| | | |
|---|---|---|
| EP | 1808362 | 5/1969 |
| EP | 0257368 | 3/1988 |
| EP | 0329460 | 8/1989 |
| EP | 0385106 | 9/1990 |
| EP | 0448930 | 10/1991 |

OTHER PUBLICATIONS

Spenlehauer et al., "Biomaterials", vol. 10 (8), Oct. 1989, pp. 557–563.
CA 102:186093k (1985).
CA 102:7723w (1984).

* cited by examiner

Primary Examiner—Kathleen Kahler Fonda
(74) Attorney, Agent, or Firm—Joseph M. Mazzarese

(57) ABSTRACT

The invention relates to certain stable microsphere compositions containing a fat, a wax or a mixture thereof; an active ingredient selected from LL-F28249α-λ compounds, 23-oxo or 23-imino derivatives of LL-F28249α-λ compounds, milbemycin compounds and avermectin compounds; an antioxidant and, optionally, an oil, a semi-soft fat, a fatty acid derivative or mixture thereof. The invention also relates to a method for introducing and maintaining levels of the active compound in the blood of warm-blooded animals for extended periods of time and for the prevention or treatment of infections and infestations caused by helminths, nematodes, acarids and endo- and ectoparasitic arthropods in warm-blooded animals by the parenteral administration of compositions of the invention.

19 Claims, No Drawings

STABLE COMPOSITIONS FOR PARENTERAL ADMINISTRATION AND THEIR USE

This application is continuation-in-part of Ser. No. 07/734,430, filed Jul. 23, 1991, now abandoned.

BACKGROUND OF THE INVENTION

Macromolecules such as LL-F28249α-λ compounds, 23-oxo and 23-imino derivatives of LL-F28249α-λ compounds, milbemycin compounds and avermectin compounds are useful for the prevention and treatment of infections and infestations caused by helminths, nematodes, acarids and endo- and ectoparasitic arthropods when parenterally administered to warm-blooded animals. Parenteral compositions are sterilized prior to administration to an animal. Gamma radiation is an effective sterilization process for eliminating microbial contaminants. However, certain macromolecules such as LL-F28249α-λ compounds, 23-oxo and 23-imino derivatives of LL-F28249α-λ compounds, milbemycin compounds and avermectin compounds degrade and lose much of their biological activity when irradiated. This destructive and degradative response to gamma radiation precludes the use of gamma radiation as a means to sterilize certain macromolecule-containing compositions.

It is an object of the present invention to provide stable compositions which can be irradiated that are useful for the prevention or treatment of infections and infestations caused by helminths, nematodes, acarids and endo- and ectoparasitic arthropods when parenterally administered to warm-blooded animals.

It is also an object of this invention to provide a method for introducing and maintaining levels of LL-F28249α-λ compounds, 23-oxo and 23-imino derivatives of LL-F28249α-λ compounds, milbemycin compounds and avermectin compounds in the blood of warm-blooded animals for extended periods of time.

SUMMARY OF THE INVENTION

The present invention relates to stable microsphere compositions which can be irradiation sterilized for parenteral administration. The compositions comprise, on a weight basis, about 20% to 95% of a fat, a wax or a mixture thereof, about 1% to 50% of an LL-F28249α-λ compound, a 23-oxo or 23-imino derivative of an LL-F28249α-λ compound, a milbemycin compound or an avermectin compound, 0 to about 30% of an oil, semi-soft fat, fatty acid derivative or mixtures thereof and about 0.001% to 10% of an antioxidant.

Surprisingly, it has been found that the microsphere compositions of the invention can be sterilized by gamma radiation without degradation of its biological activity. Also unexpectedly, the microsphere compositions can achieve an effective sustained release effect of the water-insoluble, complex macrolides.

DETAILED DESCRIPTION OF THE INVENTION

In accordance with the present invention, the stable, slow release microsphere compositions comprise an LL-F28249α-λ compound, a 23-oxo or 23-imino derivative of an LL-F28249α-λ compound, a milbemycin compound or an avermectin compound; a fat, a wax or a mixture thereof; an antioxidant and, optionally, an oil, a semi-soft fat, a fatty acid derivative or a mixture thereof. The microsphere compositions are parenterally administered by dispersion in a pharmaceutically and pharmacologically acceptable liquid vehicle. The invention also provides a method for introducing and maintaining blood levels of an LL-F28249α-λ compound, a 23-oxo or 23-imino derivative of an LL-F28249α-λ compound, a milbemycin compound or an avermectin compound in warm-blooded animals for an extended period of time.

Preferred stable microsphere compositions of the invention comprise, on a weight basis, about 50% to 90% of a fat, a wax or a mixture thereof; about 5% to 25% of an LL-F28249α-λ compound, a 23-oxo or 23-imino derivative of an LL-F28249α-λ compound, a milbemycin compound or an avermectin compound; 0 to about 20% of an oil, a semi-soft fat, a fatty acid derivative or mixtures thereof and about 0.01% to 5% of an antioxidant.

The compounds designated LL-F28249α-λ are (collectively) isolates from the fermentation broth of the microorganism Streptomyces cyaneogriseus subspecies noncyanogenus, deposited in the NRRL under deposit accession No. 15773. The method for preparation of LL-F28249α is disclosed in U.S. Pat. No. 5,106,994 and its continuation, U.S. Pat. No. 5,169,956, which are incorporated herein by reference thereto.

The LL-F28249α-λ compounds are represented by the following structural formula:

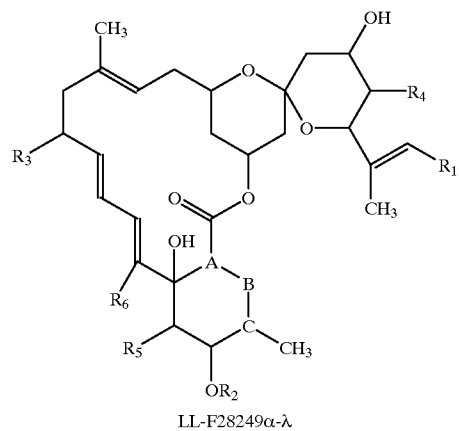

LL-F28249α-λ

| LL-F28249 | $R_1$ | $R_2$ | $R_3$ | $R_4$ | $R_5$ | $R_6$ | $R_5 + R_6$ | A—B | B—C |
|---|---|---|---|---|---|---|---|---|---|
| alpha | $CH(CH_3)_2$ | H | $CH_3$ | $CH_3$ | | | —O—$CH_2$— | CH—CH | CH=C |
| beta | $CH_3$ | H | $CH_3$ | $CH_3$ | | | —O—$CH_2$— | CH—CH | CH=C |
| gamma | $CH_3$ | $CH_3$ | $CH_3$ | $CH_3$ | | | —O—$CH_2$ | CH—CH | CH=C |
| delta | $CH_3$ | $CH_3$ | $CH_3$ | $CH_3$ | OH | $CH_2OH$ | | CH—CH | CH=C |

-continued

| LL-F28249 | $R_1$ | $R_2$ | $R_3$ | $R_4$ | $R_5$ | $R_6$ | $R_5 + R_6$ | A—B | B—C |
|---|---|---|---|---|---|---|---|---|---|
| epsilon | $CH(CH_3)_2$ | H | H | $CH_3$ | | | —O—$CH_2$ | CH—CH | CH=C |
| zeta | $CH_2CH_3$ | H | $CH_3$ | $CH_3$ | | | —O—$CH_2$ | CH—CH | CH=C |
| eta | $CH(CH_3)_2$ | H | $CH_3$ | $CH_3$ | | | —O—$CH_2$ | C=CH | CH—CH |
| theta | $CH(CH_3)_2$ | H | $CH_3$ | $CH_2CH_3$ | | | —O—$CH_2$ | CH—CH | CH=C |
| iota | $CH(CH_3)_2$ | H | $CH_2CH_3$ | $CH_3$ | | | —O—$CH_2$— | CH—CH | CH=C |
| kappa | $CH_3$ | $CH_3$ | $CH_3$ | $CH_3$ | H | $CH_3$ | | CH—CH | CH=C |
| lambda | $CH(CH_3)_2$ | $CH_3$ | $CH_3$ | $CH_3$ | | | —O—$CH_2$ | CH—CH | CH=C |

The 23-oxo and 23-imino derivatives of LL-F28249α-λ compounds, useful in the stable microsphere compositions of this invention, are disclosed in U.S. Pat. No. 4,916,154 which is incorporated herein by reference thereto.

A preferred LL-F28249α-λ compound and 23-imino derivative of an LL-F28249α-λ compound useful in the microsphere compositions of this invention have the following structural formulas:

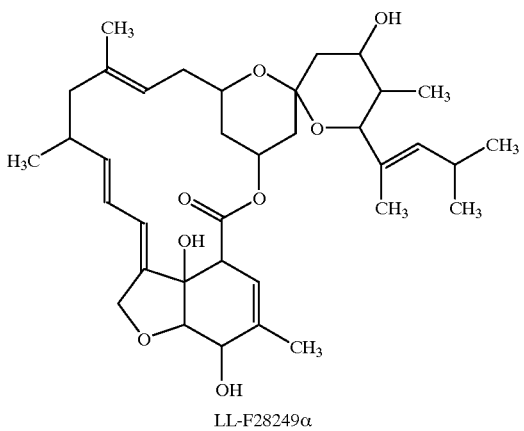

LL-F28249α and

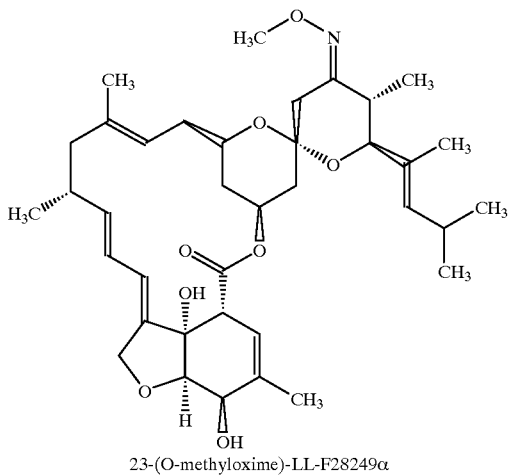

23-(O-methyloxime)-LL-F28249α

The wax of the present invention may be defined as set forth in Hawley's *The Condensed Chemical Dictionary*, Eleventh Edition, as a low-melting organic mixture or compound of high molecular weight, solid at room temperature and generally similar in composition to fats and oils except that it contains no glycerides. Some are hydrocarbons; others are esters of fatty acids and alcohols. These compounds include saturated or unsaturated long chain $C_{10}$–$C_{24}$ fatty acids, alcohols, esters, salts, ethers or mixtures thereof. They are classed among the lipids. Waxes are thermoplastic, but since they are not high polymers, they are not considered in the family of plastics. Common properties are water repellency; smooth texture; nontoxicity; freedom from objectionable odor and color. They are combustible and have good dielectric properties. They are soluble in most organic solvents and are insoluble in water. The major types are as follows:

I. Natural
 1. Animal (beeswax, lanolin, shellac wax, Chinese insect wax)
 2. Vegetable (carnauba, candelilla, bayberry, sugar cane)
 3. Mineral
  (a) Fossil or earth waxes (ozocerite, ceresin, montan)
  (b) petroleum waxes (paraffin, microcrystalline) (slack or scale wax)

II. Synthetic
 1. Ethylenic polymers and polyol ether-esters (Carbowax®, registered trademark of Union Carbide Corp., New York, N.Y.)
 2. Chlorinated naphthalenes
 3. Hydrocarbon type via Fischer-Tropsch synthesis The fat of the invention may be defined as set forth in Hawley's *The Condensed Chemical Dictionary*, Eleventh Edition, as a glyceryl ester of higher fatty acids such as stearic and palmitic. Such esters and their mixtures are solids at room temperatures and exhibit crystalline structure. Lard and tallow are examples. The term "fat" usually refers to triglycerides specifically, whereas "lipid" is all-inclusive.

The fat is preferably a hard fat composed of mono-, di- or triglyceryl esters of long chain $C_{10}$–$C_{24}$ fatty acids. The mono-, di- or triglycerides are composed predominantly of stearates, palmitates, laurates, linoleates, linolenates, oleates, and residues or mixtures thereof; those having melting points greater than 50° C. are most preferred (i.e. a "higher melting" fat). Glyceryl tristearate is a most preferred fat. Additionally, lipophilic salts of fatty acids such as magnesium stearate and the like are also suitable.

The oil, semi-soft fat or fatty acid derivative of the invention are agents which are soluble in the molten hard fat and which accelerate physical transformation of the hard fat crystal from less stable forms to more stable forms at or near room temperature after the molten hard fat or wax solidifies. Preferably, the oil or semi-soft fat may include mixtures or relatively pure forms of mono-, di- or triglyceryl esters with short to medium fatty acid chain lengths, that is, $C_2$ to $C_{18}$. Semi-soft fats refer to glyceryl esters having melting points at or near room temperature. Fatty acid derivatives include short and medium chain length fatty acids, alcohols, esters, ethers, salts or mixtures thereof; those having melting points less than 50° C. are most preferred (i.e., a "lower melting" fat). Glyceride oils and semi-soft fats are particularly suitable because they are physiological constituents of the body and are biocompatible and biodegradable.

The antioxidant of the invention may be defined as set forth in Hawley's *The Condensed Chemical Dictionary*, Eleventh Edition, as an organic compound added to rubber, natural fats and oils, food products, gasoline and lubricating oils to retard oxidation, deterioration, rancidity and gum formation, respectively. Rubber antioxidants are commonly of an aromatic amine type, such as di-β-naphthyl-p-phenylenediamine and phenyl-β-naphthylamine. Many antioxidants are substituted phenolic compounds (butylated hydroxyanisole, di-tertbutyl-p-cresol and propyl gallate). Food antioxidants are effective in very low concentration and not only retard rancidity but protect the nutritional value by minimizing the breakdown of vitamins and essential fatty acids.

Surprisingly, the antioxidant of the invention allows the present microsphere compositions to be sterilized with gamma radiation and maintain shelf life without significant loss of biological activity. In the absence of an antioxidant, macromolecules such as LL-F28249α-λ compounds, 23-oxo and 23-imino derivatives of LL-F28249α-λ compounds, milbemycin compounds and avermectin compounds degrade and lose much of their biological activity when irradiated. Antioxidants suitable for use in the microsphere compositions of the invention include, but are not limited to, butylated hydroxytoluene, butylated hydroxyanisole, tert-butylhydroxyquinone, propyl gallate, a-tocopherol, 6-ethoxy-1,2-dihydro-2,2,4-trimethylquinoline and the like, with butylated hydroxytoluene being a preferred antioxidant.

The stable microspheres of the invention are dispersed in a pharmaceutically and pharmacologically acceptable liquid to obtain a slow release composition for parenteral administration. The vehicle may be aqueous buffered systems or oil systems. The oil system may be derived from animal or vegetable sources or be synthetic. Preferred vehicles include neutral mono-, di-or triglyceride liquid or mixtures thereof. A neutral oil is one containing no residual acid. Vehicles suitable for use in the compositions of this invention include aqueous systems such as buffered salines; organic solvents such as glycols and alcohols; and water immiscible liquids such as oils, depending upon the solubility of the active ingredient being administered.

Excipients such as thickening agents, surfactants, salts, buffers or mixtures thereof may be included in the compositions of the invention. The amounts of said excipients suitable for use in the invention range from about 0.1% to 20% on a weight basis.

Blood levels of the LL-F28249α-λ compounds, 23-oxo and 23-imino derivatives of LL-F28249α-λ compounds, milbemycin compounds and avermectin compounds may be obtained and maintained for extended periods of time by injecting animals with the compositions of the invention in a suitable vehicle. Unexpectedly, the water-insoluble macrolide antibiotics can be effectively delivered from the microsphere formulation for a sustained release effect.

Maintained blood levels of the active compounds are associated with the protection or treatment of warm-blooded animals against infections and infestation by helminths, nematodes, acarids and endo- and ectoparasitic arthropods. Maintaining the blood levels is an indication of the slow release of the active ingredient. The invention includes the use of the compositions herein to introduce and maintain levels of LL-F28249α-λ compounds, 23-oxo and 23-imino derivatives of LL-F28249α-λ compounds, milbemycin compounds and avermectin compounds in the blood stream of animals.

When parenterally administered, the compositions of this invention are highly effective for protecting or treating warm-blooded animals such as dogs, cats, cattle, sheep, horses, swine, goats, poultry and the like against infection and infestation by helminths, nematodes, acarids and endo- and ectoparasitic arthropods.

Helminthiasis is a widespread disease found in many animals and is responsible for significant economic losses throughout the world. Among the helminths most frequently encountered are the group of worms referred to as nematodes. The nematodes are found in the intestinal tract, heart, lungs, blood vessels and other body tissues of animals and are a primary cause of anemia, weight loss and malnutrition in the infected animals. They do serious damage to the walls and tissue of the organs in which they reside and, if left untreated, may result in death to the infected animals.

The nematodes most commonly found to be the infecting agents of ruminants include Haemonchus and Ostertagia generally found in the abomasum; Cooperia, Trichostrongylus and Nematodirus generally found in the intestinal tract, and Dictyocaulus found in the lungs. In non-ruminant animals important nematodes include Toxocara and Ancylostoma in the intestine and Dirofilaria in the heart of dogs; Ascaris in the intestine of swine; Ascaridia and Heterakis in the intestine of poultry; and large and small strongyles in equines. Treatment of animals to prevent infestation thereof by the above nematodes or to reduce or control the proliferation of these infecting agents in animals is thus an important and desirable advantage of the present invention.

Besides controlling helminths and nematodes, the present invention also controls arthropod endo-parasitic infestations such as cattle grub and ecto-parasitic infestations such as psoroptic mange and cattle ticks.

The microspheres of the invention may be prepared by incorporating the active ingredient, antioxidant and other excipients with a molten fat, wax or mixture thereof, optionally admixing the oil, semi-soft fat, fatty acid derivative or mixtures thereof, and then forming microspheres of the resulting mixture by a variety of techniques such as emulsifying or atomizing the mixture or by processing the mixture of ingredients and molten fat, wax or mixture thereof mechanically and cooling, for example, utilizing a centrifugal disc.

Alternatively, the mixture of active ingredients, antioxidants, excipients and fat, waxes and mixtures thereof and oil, may be cooled to give a solid which may then be processed by procedures such as milling, grinding and the like. The microspheres, preferably fat microspheres, may be up to 1,000 microns in diameter, with a weight average size range of about 25 microns to 300 microns being preferred for parenteral administration.

In order to facilitate a further understanding of the invention, the following examples are presented primarily for the purpose of illustrating more specific details thereof. The invention is not to be deemed limited thereby except as defined in the claims.

EXAMPLE 1

Preparation of Microspheres for the Parenteral Administration of 23-(O-methyloxime)-LL-F28249α

Glyceryl tristearate (32.526 g) and triglyceride oil (3.614 g) are heated to 85°–90° C. in a beaker on a hot plate, 23-(O-methyloxime)-LL-F28249α (5.0 g) and butylated hydroxytoluene (0.46 g) are added with constant stirring until the 23-(O-methyloxime)-LL-F28249α and butylated hydroxytoluene dissolve, This solution is then poured into a feed bowl of a laboratory spray priller. The feed bowl, feed lines, air supply lines and a two fluid spray atomizing nozzle are maintained at 85°–90° C. with hot air. Fluid feed to the nozzle is assisted with a 1 psi pressure head and the atomizing air pressure is 10 psi. The atomized mixture is collected from the outlet of the prilling chamber with a cyclone separator. The microspheres are then sieved to remove microspheres larger than 180 microns. Those microspheres which are larger than 180 microns are collected for recycling.

The microspheres obtained using the above procedure have the following composition.

|  | % w/w |
|---|---|
| 23-(O-methyloxime)-LL-F28249α | 12.0 |
| glyceryl tristearate | 78.2 |
| triglyceride oil | 8.7 |
| butylated hydroxytoluene (BHT) | 1.1 |

EXAMPLE 2

Stability of Microspheres to Irradiation

The microsphere compositions listed below are placed in 20 mL serum vials, two of which are flushed with dry nitrogen gas to remove oxygen. The vials are then closed with elastomeric septums and crimped aluminum caps. Next, the microspheres are irradiated at ambient temperature with cobalt 60 (gamma radiation) with the dosages indicated in Table I below. The microspheres are extracted into acetonitrile/water (1:1 and analyzed for 23-(O-methyloxime)-LL-F28249α by high performance liquid chromatography. The results of this experiment are summarized below in Table I.

Microsphere Compositions

| Ingredient | A1 (% w/w) | B2 (% w/w) |
|---|---|---|
| 23-(O-methyloxime)-LL-F28249α | 12.0 | 12.0 |
| glyceryl tristearate | 79.2 | 78.2 |
| medium chain triglyceride oil | 8.8 | 8.7 |
| butylated hydroxytoluene | 0 | 1.1 |

[1]Prepared by the procedure of Example 1, except that butylated hydroxytoluene is not utilized.
[2]Microsphere composition prepared in Example 1.

TABLE 1

Percent Recovery of 23-(O-methyloxime)-LL-F28249α
From Microsphere Compositions After Irradiation

| | Composition | | | |
|---|---|---|---|---|
| | A | | B | |
| Exposure (Mrad) | Air | Nitrogen | Air | Nitrogen |
| 0 | 94.5 | 94.5 | 96.5 | 96.5 |
| 0.55 | 68.5 | 92.5 | 95.0 | 96.5 |
| 2.1 | 27.5 | 90.5 | 96.0 | 95.0 |

This experiment demonstrates that the active ingredient present in microspheres without BHT degrades when irradiated with gamma radiation in either air or nitrogen atmospheres and that the active ingredient is stable when BHT is present in the formulation.

EXAMPLE 3

Sustained Release of Microsphere Compositions of the Invention in Dogs

Dogs are divided into groups of three or four animals each. Throughout the test, all dogs are fed the same ration. The dogs are weighed and injected with a composition containing the microsphere composition of Example 1 (1 g) mixed with a 2.5% methylcellulose in normal saline solution (2 mL) in amounts required to obtain the desired dose of active ingredient per kg of body weight. 23-(O-methyloxime) -LL-F28249α levels in the blood of the dogs is determined by HPLC techniques periodically. The results of this experiment, which are summarized in Table II below, demonstrate the effectiveness of the microsphere compositions of the invention for introducing and maintaining 23-(O-methyloxime)-LL-F28249α levels in the blood.

TABLE II

Average Serum 23-(O-methyloxime)-LL-F28249α
Concentration (ppb by HPLC) For Dog Experiments

| Time | Dose (mg/kg) | |
|---|---|---|
| (days) | 5[1] | 1.7[2] |
| 1 | 111 | 39 |
| 3 | 197 | 80 |
| 8 | 340 | 100 |
| 15 | 133 | 50 |
| 21 | 80 | 29 |
| 28 | 68 | 21 |
| 35 | 51 | 14 |
| 42 | 33 | 10 |
| 49 | 20 | 7 |

[1]three dogs
[2]four dogs

EXAMPLE 4

Evaluation of the Half-life of the Release of the Microsphere Compositions of the Invention Four dogs are injected with a microsphere formulation containing 23-(O-methyloxime)-LL-F28249α at a dosage level of 3.5 mg/kg. The formulation is prepared as follows: Glyceryl tristearate (8.8 g) is melted on a hot plate in a 100 mL beaker including a stir bar, the BHT (2.25 mg) is added and dispersed/melted, and then the 23-(O-methyloxime)-LL-F28249α (1.0 g) is added and stirred until dissolved into the glyceryl tristearate. Once prepared, this molten material is quickly transferred to the liquid feed vessel of the custom laboratory priller to prepare the microspheres. The microspheres have the following formulation.

|  | Amount |
|---|---|
| 23-(O-methyloxime)-LL-F28249α | 1.0 g |
| glyceryl tristearate | 8.8 g |
| butylated hydroxytoluene (BHT) | 2.25 mg |

A laboratory prilling apparatus is constructed which provided for prefiltered air into a tower where the spray gelation takes place. Spray gelation (prilling) is done with a two-fluid nozzle (air atomization) to form liquid droplets which rapidly solidify in the ambient temperature air of the prilling tower. Microspheres are collected from the spraying tower with a cyclone separator. After collection the batch is sieved into three size ranges.

The ranges and recoveries are as follows:

| | |
|---|---|
| >180 micron | 1.76 g |
| 180–90 micron | 3.16 g |
| <90 micron | 3.29 g |
| | 8.21 g |

Aliquots for animal testing in the desired size range are weighed into 10 or 20 mL serum vials. The loaded serum vials are flushed with dry nitrogen through an 18 G, 1.5" hypodermic needle directed into the bottom of the vial. Samples are irradiated at room temperature at a dose of approximately 0.5 Mrad.

The diluent for the microsphere is 2% methylcellulose in normal saline. After the methylcellulose is dissolved and brought to a concentration of about 2%, sodium chloride is added to a concentration of 0.085% (Normal Saline). This solution is filtered through 0.2 micron membrane filter into autoclaved serum vials. On the day of the test in dogs, the vehicle is added to the irradiated microspheres; 9.2 mL of vehicle is added to 2 grams of microspheres (90–180 micron diameter) for a total volume of approximately 11.2 mL, which gives a concentration of 23-(O-methyloxime)-LL-F28249α of approximately 17.5 mg/mL.

Samples of microspheres are analyzed for 23-(O-methyloxime)-LL-F28249α content by extraction (about 16 hours) in acetonitrile. Extracts are analyzed for 23-(O-methyloxime)-LL-F28249α content by HPLC.

On the day of treatment (day 0), the microspheres are reconstituted by adding 9.08 mL of diluent to the vial containing 2 g of microspheres to make a total volume of 11.2 mL.

Following injections, the dogs are observed for 6 hours and then daily through day 32. From day 32 until day 84, observations are reduced to 3 per week. Then for the balance of the study, dogs are checked weekly.

Twenty milliliters of blood are taken from the jugular vein of dogs in group 1 on days 0, 1, 2, 4, 7, 10 and 14. From day 14 on, blood is collected weekly with the last bleeding on day 175. From day 63 through the end of the study, the amount drawn is increased to 30 mL and the serum frozen in two vials of 5 and 10 mL each.

Maximum serum levels of 20–45 ppb of 23-(O-methyloxime)-LL-F28249α are reached on days 7–14. The levels gradually decrease until 175 days, when they are 1.2, 5.5, 8.3 and 13 ppb of 23-(O-methyloxime)-LL-F28249α in the four dogs. The apparent half-life of release from the microspheres is observed to be approximately 73 days.

Results of the analysis of the serum levels are presented in Table III below.

TABLE III 23-(O-methyloxime-LL-F28249α Serum Levels From Dogs Injected With 10% 23-(O-methyloxime)-LL-F28249α Microspheres at 3.5 mg/kg

| | 23-(O-methyloxime)-LL-F28249α Serum Levels (ppb) | | | | | | | |
|---|---|---|---|---|---|---|---|---|
| | Days post-treatment | | | | | | | |
| Dog No. | 0 | 1 | 2 | 4 | 7 | 10 | 14 | 21 |
| 1 | <5 | 13.0 | 27 | 26 | 30 | 43 | 45 | 44.0 |
| 2 | <5 | 8.4 | 12 | 11 | 20 | 14 | 12 | 6.4 |
| 3 | <5 | 13.0 | 20 | 40 | 34 | 25 | 44 | 32.0 |
| 4 | <5 | 8.0 | 15 | 36 | 39 | 24 | 27 | 16.0 |

| Dog No. | 28 | 35 | 42 | 49 | 56 | 63 | 70 | 77 |
|---|---|---|---|---|---|---|---|---|
| 1 | 36.0 | 37.0 | 40.0 | 40.0 | 32 | 30 | 22 | 25 |
| 2 | 4.9 | 3.9 | 2.9 | 3.0 | <5 | <5 | 21 | <5 |
| 3 | 31.0 | 32.0 | 31.0 | 24.0 | 17 | 16 | 13 | 16 |
| 4 | 19.0 | 20.0 | 22.0 | 19.0 | 12 | 12 | 11 | 12 |

| Dog No. | 84 | 98 | 112 | 126 | 140 | 147 | 161 | 175 |
|---|---|---|---|---|---|---|---|---|
| 1 | 21 | 14.0 | 13.0 | 19.0 | 12.0 | 8.1 | 6.6 | 5.5 |
| 2 | <5 | 1.5 | 1.4 | 1.5 | 1.2 | 1.2 | 1.0 | 1.2 |
| 3 | 14 | 10.0 | 12.0 | 12.0 | 15.0 | 8.4 | 9.5 | 8.3 |
| 4 | 11 | 9.0 | 11.0 | 9.1 | 7.9 | 8.6 | 11.0 | 13.0 |

We claim:

1. A microsphere composition comprising on a weight basis about 20% to 95% of a higher melting fat, a wax or a mixture thereof; about 1% to 50% of a compound dissolved into said higher melting fat, wax or mixture thereof, said compound selected from the group consisting of an LL-F28249α-λ, a 23-oxo or 23-imino derivative of an LL-F28249α-λ, a inilbemycin and an avermectin; 0 to about 30% of an oil, a semi-soft fat, a lower melting fatty acid, a lower melting fatty acid alcohol, a lower melting fatty acid ester, a lower melting fatty acid ether, a salt of a lower melting fatty acid or a mixture thereof; and about 0.001% to 10% of an antioxidant.

2. The microsphere composition according to claim 1 comprising on a weight basis about 50% to 90% of the higher melting fat, the wax or the mixture thereof; about 5% to 25% of the compound; 0 to about 20% of the oil, the semi-soft fat, the lower melting fatty acid, the lower melting fatty acid alcohol, the lower melting fatty acid ester, the lower melting fatty acid ether, the salt of the lower melting fatty acid or the mixture thereof; and about 0.01% to 5% of the antioxidant.

3. The microsphere composition according to claim 2 wherein the compound is 23-(O-methyloxime)-LL-F28249α.

4. The microsphere composition according to claim 2 wherein the compound is LL-F28249α.

5. The microsphere composition according to claim 2 wherein the higher melting fat is glyceryl tristearate, the oil is a neutral triglyceride oil and the antioxidant is butylated hydroxytoluene.

6. The microsphere composition according to claim 2 wherein the composition further comprises on a weight basis about 0.1% to 20% of a surfactant, a salt, a buffer or a mixture thereof.

7. The microsphere composition according to claim 2 wherein the weight average particle of the microsphere composition is in a range of about 25 microns to 300 microns.

8. The microsphere composition according to claim 2 further comprising a pharmaceutically and pharmacologically acceptable liquid vehicle in which the microspheres are dispersed for parenteral administration and slow release.

9. A method for protecting or treating warm-blooded animals against infection or infestation by helminths, nematodes, acarids or endo- or ecto-parasitic arthropods which comprises parenterally administering to the animal a microsphere composition comprising on a weight basis about 20% to 95% of a higher melting fat, a wax or a mixture thereof; about 1% to 50% of a compound selected from the group consisting of an LL-F28249α-λ, a 23-oxo or 23-imino derivative of an LL-F28249α-λ, a milbemycin and an avermectin; 0 to about 30% of an oil, a semi-soft fat, a lower melting fatty acid, a lower melting fatty acid alcohol, a lower melting fatty acid ester, a lower melting fatty acid ether, a salt of a lower melting fatty acid or a mixture thereof; and about 0.001% to 10% of an antioxidant; wherein the microsphere is dispersed in a pharmaceutically and pharmacologically acceptable liquid vehicle.

10. The method according to claim 9 wherein the microsphere comprises on a weight basis about 50% to 90% of the higher melting fat, the wax or the mixture thereof; about 5% to 25% of the compound; 0 to about 20% of the oil, the semi-soft fat, the lower melting fatty acid, the lower melting fatty acid alcohol, the lower melting fatty acid ester, the lower melting fatty acid ether, the salt of the lower melting fatty acid or the mixture thereof; and about 0.01% to 5% of the antioxidant.

11. The method according to claim 10 wherein the compound is LL-F28249α or 23-(O-methyloxime)-LL-F28249α.

12. The method according to claim 10 wherein the higher melting fat is glyceryl tristearate, the oil is a neutral triglyceride oil, the antioxidant is butylated hydroxytoluene, and the microsphere vehicle is a methylcellulose and saline mixture.

13. The method according to claim 10 wherein the microsphere additionally comprises on a weight basis about 0.1% to 20% of a surfactant, a salt, a buffer or a mixture thereof.

14. The method according to claim 10 wherein the weight average particle size of the microsphere composition is in a range of about 25 microns to 300 microns.

15. The method according to claim 9 wherein the warm-blooded animal is selected from the group consisting of dogs, cats, cattle, sheep, horses, swine, poultry and goats.

16. A method for introducing and maintaining blood levels of a compound selected from the group consisting of an LL-F28249α-λ, a 23-oxo or 23-imino derivative of an LL-F28249α-λ, a milbemycin and an avermectin in a warm-blooded animal which comprises parenterally administering to the animal a microsphere composition comprising on a weight basis about 20% to 95% of a higher melting fat, a wax or a mixture thereof; about 1% to 50% of the compound; 0 to about 30% of an oil, a semi-soft fat, a lower melting fatty acid, a lower melting fatty acid alcohol, a lower melting fatty acid ester, a lower melting fatty acid ether, a salt of a lower melting fatty acid or a mixture thereof; and about 0.001% to 10% of an antioxidant; wherein the microsphere is dispersed in a pharmaceutically and pharmacologically acceptable liquid vehicle.

17. The method according to claim 16 wherein the microsphere comprises on a weight basis about 50% to 90% of the higher melting fat, the wax or the mixture thereof; about 5% to 25% of the compound; 0 to about 20% of the oil, the semi-soft fat, the lower melting fatty acid, the lower melting fatty acid alcohol, the lower melting fatty acid ester, the lower melting fatty acid ether, the salt of the lower melting fatty acid or the mixture thereof; and about 0.01% to 5% of the antioxidant.

18. The method according to claim 17 wherein the compound is LL-F28249α or 23-(O-methyloxime)-LL-F28249α.

19. The method according to claim 17 wherein the higher melting fat is glyceryl tristearate, the oil is a neutral triglyceride oil, the antioxidant is butylated hydroxytoluene, and the microsphere vehicle is a methylcellulose and saline mixture.

* * * * *